(12) United States Patent
Hiles

(10) Patent No.: US 8,454,678 B2
(45) Date of Patent: Jun. 4, 2013

(54) PROSTHETIC IMPLANTS INCLUDING ECM COMPOSITE MATERIAL

(75) Inventor: Michael Hiles, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 519 days.

(21) Appl. No.: 11/378,690

(22) Filed: Mar. 17, 2006

(65) Prior Publication Data

US 2006/0210597 A1    Sep. 21, 2006

Related U.S. Application Data

(60) Provisional application No. 60/663,549, filed on Mar. 19, 2005.

(51) Int. Cl.
*A61F 2/06* (2006.01)

(52) U.S. Cl.
USPC .................... 623/1.24; 623/1.26; 623/2.14

(58) Field of Classification Search
USPC .................. 435/325, 373, 377, 383, 395, 384
See application file for complete search history.

(56) References Cited

U.S. PATENT DOCUMENTS

| | | | |
|---|---|---|---|
| 4,218,782 A | 8/1980 | Rygg | |
| 4,361,552 A | 11/1982 | Baur | |
| 4,902,508 A | 2/1990 | Badylak et al. | |
| 4,956,178 A | 9/1990 | Badylak et al. | |
| 5,156,620 A | 10/1992 | Pigott | |
| 5,275,826 A | 1/1994 | Badylak et al. | |
| 5,281,422 A | 1/1994 | Badylak et al. | |
| 5,411,552 A | 5/1995 | Andersen et al. | |
| 5,554,389 A | 9/1996 | Badylak et al. | |
| 5,607,465 A | 3/1997 | Camilli | |
| 5,695,998 A | 12/1997 | Badylak et al. | |
| 5,716,394 A | 2/1998 | Bruchman et al. | |
| 5,733,337 A | 3/1998 | Carr et al. | |
| 5,762,600 A | 6/1998 | Bruchman et al. | |
| 5,776,182 A | 7/1998 | Bruchman et al. | |
| 5,855,601 A | 1/1999 | Bessler et al. | |
| 5,855,620 A | 1/1999 | Bishopric et al. | |
| 5,879,383 A | 3/1999 | Bruchman et al. | |

(Continued)

FOREIGN PATENT DOCUMENTS

| | | |
|---|---|---|
| EP | 0809691 | 1/2003 |
| WO | WO 95/22301 A | 8/1995 |

(Continued)

OTHER PUBLICATIONS

Badylak, et al. "Small Intestinal Submucosa: A Substrate for in vitro Cell Growth" *Journal of Biomaterials Sci. Polymer Edn* 1998; 8(9): 863-878.

(Continued)

*Primary Examiner* — David Isabella
*Assistant Examiner* — Suba Ganesan
(74) *Attorney, Agent, or Firm* — Woodard, Emhardt, Moriarty, McNett & Henry LLP

(57) ABSTRACT

Described are preferred prosthetic valve devices including a first extracellular matrix material having a second extracellular matrix material deposited thereon. The preferred materials are made by culturing cells in contact with an extracellular matrix graft material in a fashion to cause the cells to biosynthesize and deposit extracellular matrix components on the material. The cells are then removed to provide the extracellular matrix composite material. In preferred embodiments, the prosthetic valve devices are configured for use in vascular applications.

32 Claims, 6 Drawing Sheets

U.S. PATENT DOCUMENTS

| | | | |
|---|---|---|---|
| 5,908,449 A | 6/1999 | Bruchman et al. | |
| 5,993,844 A | 11/1999 | Abraham et al. | |
| 6,099,567 A | 8/2000 | Badylak et al. | |
| 6,110,201 A | 8/2000 | Quijano et al. | |
| 6,126,686 A | 10/2000 | Badylak et al. | |
| 6,168,614 B1 | 1/2001 | Andersen et al. | |
| 6,200,336 B1 | 3/2001 | Pavcnik et al. | |
| 6,206,931 B1 | 3/2001 | Cook et al. | |
| 6,287,334 B1 | 9/2001 | Moll et al. | |
| 6,299,637 B1 | 10/2001 | Shaolian et al. | |
| 6,331,319 B1 | 12/2001 | Badylak et al. | |
| 6,379,710 B1 | 4/2002 | Badylak | |
| 6,485,723 B1 | 11/2002 | Badylak et al. | |
| 6,508,833 B2 | 1/2003 | Pavcnik et al. | |
| 6,576,618 B1 | 6/2003 | Herndon et al. | |
| 6,582,462 B1 | 6/2003 | Andersen et al. | |
| 6,669,724 B2 * | 12/2003 | Park et al. | 623/1.24 |
| 6,716,241 B2 | 4/2004 | Wilder et al. | |
| 6,752,828 B2 | 6/2004 | Thornton | |
| 6,821,107 B1 * | 11/2004 | Hara et al. | 425/397 |
| 2001/0011187 A1 | 8/2001 | Pavcnik et al. | |
| 2001/0039450 A1 | 11/2001 | Pavcnik et al. | |
| 2001/0051824 A1 | 12/2001 | Hopkins et al. | |
| 2002/0028233 A1 * | 3/2002 | Dimitrijevich | 424/447 |
| 2002/0103542 A1 * | 8/2002 | Bilbo | 623/23.72 |
| 2002/0123800 A1 | 9/2002 | Taheri et al. | |
| 2002/0138137 A1 * | 9/2002 | Cox | 623/2.13 |
| 2002/0188348 A1 | 12/2002 | DiMatteo et al. | |
| 2003/0036794 A1 | 2/2003 | Ragheb et al. | |
| 2003/0064056 A1 | 4/2003 | Badylak et al. | |
| 2003/0072741 A1 | 4/2003 | Berglund et al. | |
| 2003/0125795 A1 | 7/2003 | Pavcnik et al. | |
| 2003/0130726 A1 | 7/2003 | Thorpe | |
| 2003/0191525 A1 | 10/2003 | Thornton | |
| 2003/0208261 A1 | 11/2003 | Thorpe et al. | |
| 2003/0216811 A1 | 11/2003 | Badylak | |
| 2004/0015230 A1 | 1/2004 | Moll et al. | |
| 2004/0049262 A1 * | 3/2004 | Obermiller et al. | 623/1.15 |
| 2004/0082989 A1 | 4/2004 | Cook et al. | |
| 2004/0098084 A1 | 5/2004 | Hartley et al. | |
| 2004/0106978 A1 | 6/2004 | Greenberg et al. | |
| 2004/0176832 A1 | 9/2004 | Hartley et al. | |
| 2004/0176833 A1 | 9/2004 | Pavcnik et al. | |
| 2004/0186558 A1 | 9/2004 | Pavcnik et al. | |
| 2004/0193253 A1 | 9/2004 | Thorpe et al. | |
| 2004/0260389 A1 | 12/2004 | Case et al. | |

FOREIGN PATENT DOCUMENTS

| | | |
|---|---|---|
| WO | WO 96/08213 | 3/1996 |
| WO | WO 99/62431 | 12/1999 |
| WO | WO 01/03750 A | 1/2001 |
| WO | WO 01/19285 | 3/2001 |
| WO | WO 02/40630 | 5/2002 |
| WO | WO 03/002165 | 1/2003 |
| WO | WO 03/070124 | 8/2003 |
| WO | WO 2004/080352 A | 9/2004 |
| WO | WO 2005/013857 A | 2/2005 |

OTHER PUBLICATIONS

Heeschen, C., et al. "Nicotine Stimulates Angiogenesis and Promotes Tumor Growth and Atherosclerosis" *Nature Medicine* (2001), vol. 7 833-839. Nature Publishing Group.

Johnson, C., et al. "Matrix Matalloproteinase-9 is Required for Adequate Angiogenic Revascularization of Ischemic Tissues—Potential Role in Capillary Branching". *Circulation Research* (2004) 94; 262-268. American Heart Association, Dallas, TX.

Lindberg, K., et al. "Porcine Small Intestinal Submucosa (SIS): A Bioscaffold Supporting in Vitro Primary Human Epidermal Cell Differentiation and Synthesis of Basement Membrane Proteins". *Burns* 27 (2001) 254-266. Elsevier Science Ltd. and ISBI.

Woods, A.M., et al. "Improved Biocompatibility of Small Intestinal Submucosa (SIS) Following Conditioning by Human Endothelial Cells". *Biomaterials* 24 (2004) 515-525. Elsevier, Ltd.

Cimini, Massimo et al., "Dermal fibroblasts cultured on small intestinal submucosa: Conditions for the formation of a neotissue". *Journal of Biomedical Materials Research*, vol. 75, No. 4, Dec. 15, 2005, pp. 895-906, Wiley, New York, NY, US.

Zeltinger, J. et al., "Development and characterization of tissue-engineered aortic valves." *Tissue Engineering*, vol. 7, No. 1, Feb. 2001, pp. 9-22.

Beier, Ulf H. et al., "Small Intestinal Submucosa Prosthetic Percutaneous Valve: Reduction of leaflet thekening with a low-profile self-centring valve frame," EuroIntervention Zupplsmsnf q00 rw-. Journal of Biomedical Materials Research 2005, 75, 895-906.

Sandusky, G.E. et al, "Histologic Findings After in Vivo Placement of Small Intestine Submucosal Vascular Grafts and Saphenous Vein Grafts in the Carotid Artery in Dogs," American Journal of Pathology, vol. 140, No. 2, 317-324 (1992).

* cited by examiner

PROSTHETIC IMPLANTS INCLUDING ECM COMPOSITE MATERIAL

The present application claims the benefit of U.S. Provisional Patent Application Ser. No. 60/663,549 filed Mar. 19, 2005 entitled "PROSTHETIC IMPLANTS INCLUDING ECM COMPOSITE MATERIAL" which is hereby incorporated by reference in its entirety.

TECHNICAL FIELD OF THE INVENTION

The present invention relates generally to medical graft materials, and in particular, to medical graft materials having extracellular matrix materials deposited thereon and formed into at least one leaflet for implantation into a bodily passage.

BACKGROUND OF THE INVENTION

A variety of extracellular matrix materials have been proposed for use in medical grafting, cell culture, and other related applications. For instance, medical grafts and cell culture materials containing submucosa derived from small intestine, stomach or urinary bladder tissues, have been proposed. See, e.g., U.S. Pat. Nos. 4,902,508, 4,956,178, 5,281,422, 5,554,389, 6,099,567 and 6,206,931. In addition, Cook Biotech Incorporated, West Lafayette, Ind., currently manufactures a variety of medical products based upon small intestinal submucosa under the trademarks SURGISIS®, STRATASIS® and OASIS®.

Medical materials derived from liver basement membrane have also been proposed, for example in U.S. Pat. No. 6,379,710. As well, ECM materials derived from amnion (see e.g. U.S. Pat. Nos. 4,361,552 and 6,576,618) and from renal capsule membrane (see WO 03/002165 published Jan. 9, 2003) have been proposed for medical and/or cell culture applications.

In addition to the above, there have been attempts to alter the surface properties of an ECM to improve its characteristics. For example, Woods et al. disclose a SIS material having improved biocompatibility by virtue of it being conditioned with human umbilical vein endothelial cells (HUVECs) (Biomaterials, (25)515-525 (2004)). To produce the conditioned SIS, HUVECs were grown for 2 weeks on SIS and then removed, leaving behind an intact basement membrane. Woods et al. suggest that the above approach could be a useful step in preparing a conditioned SIS that has certain biological advantages over a native SIS.

Similarly, Lindberg et al. teach that human epidermal cells, fibroblasts (human and mouse 3T3/J2), or a combination thereof, deposit several basement membrane proteins including fibronectin, collagen types IV and VII, and laminin when seeded onto a SIS matrix (*Burns*, (27)254-266 (2001)). In this regard, Lindberg et al. teach that SIS can support attachment, migration and/or proliferation and differentiation of both epidermal cells and fibroblasts, and that these cells can alter the SIS matrix by depositing basement membrane components onto SIS.

International PCT Patent Application No. WO 02/40630 (Amiel) provides a matrix which is decellularized and then reseeded with any of a variety of cells, most notably endothelial cells and fibroblasts. Amiel maintains that acellular matrices seeded with human saphenous vein endothelial cells (HSVECs) are able to withstand a hydrostatic pressure up to 900 mmHg without breaking or leaking and that a confluent layer of HSVECs on the luminal side of the acellular matrix is achieved. Moreover, Amiel suggest that the HSVECs are able to deposit VEGF, prostaglandin F1α, and nitric oxide onto the matrix. Such proteins are thought to contribute to the improvement of biological properties of the scaffold.

Despite work in these areas, there remain needs for alternative and improved medical materials, as well as methods and devices related to these materials. The present invention addresses these needs.

SUMMARY OF THE INVENTION

In one aspect, the present invention provides a prosthetic valve device for implantation in a bodily passage. The valve device comprises an artificial valve comprising at least one leaflet formed with an extracellular matrix composite including a first extracellular matrix material having a surface, and a second, biosynthetically-deposited extracellular matrix material on said surface.

The present invention further provides a method for preparing a prosthetic valve device. The method comprises providing a first extracellular matrix material having a surface and culturing cells under in vitro conditions to secrete a second extracellular matrix material on said surface. The second material is transferred to said surface to form an extracellular matrix composite, which can be isolated in acellular form and formed into at least one leaflet.

Further provided by the invention is a method for treating a patient. The method comprises providing a prosthetic valve device of the invention and implanting the valve device into a bodily passage of the patient.

Additional embodiments as well as features and advantages of the invention will be apparent from the descriptions herein.

DESCRIPTION OF THE PREFERRED EMBODIMENTS

Figure 1A:
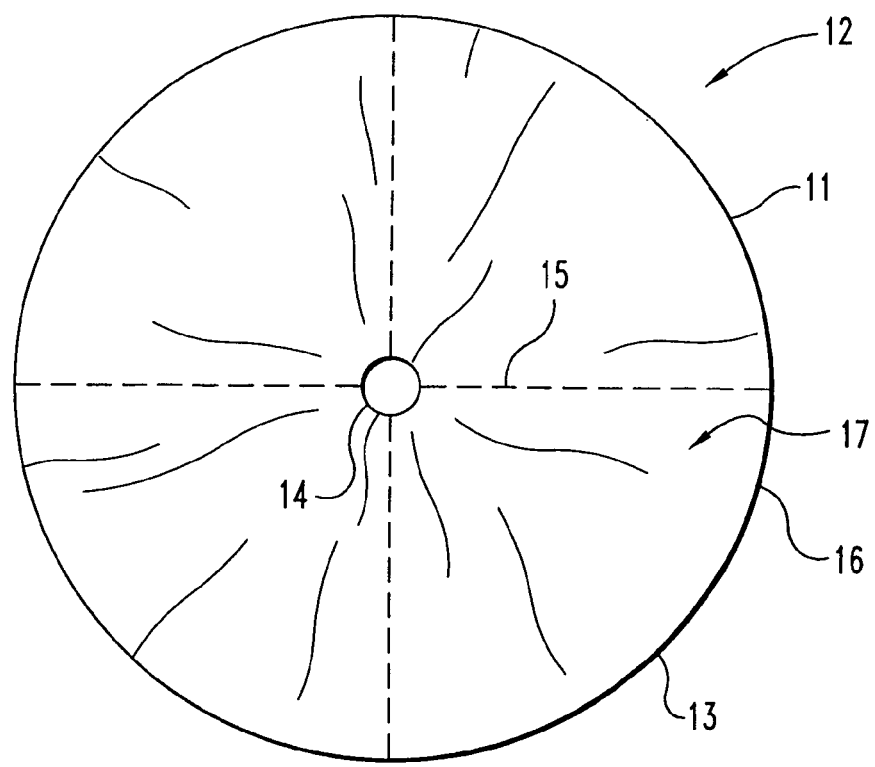
FIG. 1A provides a perspective view of a sheet of an extracellular matrix composite from which four fameless prosthetic valve devices of the invention may be obtained. The extracellular matrix composite includes a first extracellular matrix material having a surface, and a second extracellular matrix material deposited on said surface.

The present invention provides a prosthetic valve device for implantation in a bodily passage. The valve device comprises at least one leaflet formed with an extracellular matrix (ECM) composite including a first extracellular matrix material having a surface, and a second, biosynthetically-deposited extracellular matrix material on said surface.

ECM composite graft materials of the invention can be manufactured in a variety of physical forms, to suit a variety of medical applications. In this regard, the configuration of the ECM composite material may be attained before or after deposition of the non-native ECM components on the ECM base material. Further, an ECM composite material can be manufactured in larger, bulk dimensions, and then divided into smaller products. Moreover, the ECM base material may provided in a naturally-derived layer form, or may itself be a manufactured article, such as a sponge or cast sheet, prepared from a naturally-derived ECM material.

The prosthetic valve devices of the invention can be implanted into a bodily passage as a frameless valve device or, alternatively, they can be attached to a frame, such as a self-expanding or otherwise expandable stents, both to form biocompatible coverings such as sleeves and to form leaflets or other valve structures (see, e.g. WO 99/62431 published Dec. 9, 1999 and WO 01/19285 published Mar. 22, 2001). In one mode of forming a valve structure, the ECM composite material can be attached to a stent in a fashion whereby it forms one, two, or more leaflets, cusps, pockets or similar structures that resist flow in one direction relative to another. In a specific application of such devices, such devices constructed as vascular valves are implanted to treat venous insufficiencies in humans, for example occurring in the legs. In an alternate approach, valves for treating these or other valve deficiencies may be surgically created without the use of a stent or other supporting structure, and are referred to herein as a "frameless prosthetic valve device."

A frameless prosthetic valve device of the invention can be adapted to provide a monocusp valve in a vein or, alternatively, it can be adapted to provide for a multicuspid valve in a vein, wherein the multicuspid valve comprises a plurality of cusps. In this respect, the frameless prosthetic valve device can be adapted to provide a monocuspid valve, a bicuspid valve, a tricuspid valve, or a quadracuspid valve in a vein.

When a monocusp leaflet configuration is utilized in the invention, the frameless prosthetic valve device having such a configuration can be dimensioned and attached in such a manner so as to allow the leaflet to extend across the entire lumen of a vein and co-apt with the opposite wall of the vein. Alternatively, two or more monocusp devices can be provided and dimensioned for separate attachment to the wall of the vein so as to co-apt with each other within the vein lumen, e.g. near the middle of the lumen.

When a multicusp leaflet configuration is utilized, the frameless prosthetic valve device will comprise at least two leaflets, wherein the at least two leaflets are attached to the vein wall in such a manner so as to allow the leaflets to co-apt within the lumen of the vein, e.g. near the center of the lumen of the vein.

Whatever configuration is utilized, it will be understood that blood flow back to the heart will pass through the co-apt line i.e., the point where the monocusp leaflet co-apts with the opposite wall of a vein or where the at least two leaflets co-apt within the lumen of the vein, e.g. near the center of the lumen. On the other hand, blood flow in the opposite direction will be restricted.

A frameless prosthetic valve device of the invention can be adapted to provide a shaped valve cusp having any suitable configuration. For example, the shaped valve cusp after implantation can have a non-planar configuration when in a closed condition. Preferably, the shaped valve cusp will have a generally concave/convex configuration when in a closed condition, as shown for example in FIG. 1C. Other configurations are contemplated for use in the invention, and can be designed through routine experimentation so as to allow for optimal blood flow back to the heart.

A frameless prosthetic valve device of the invention can be constructed so as to have predetermined dimensions at its base, top edge, and diverging sides, such that the prosthesis is adapted to provide a valve function in a vein or other vessel of a specific diameter. For example, the dimensions of the prosthesis can be selected so as to render the device suitable for providing a valve function in a vein or other vessel having an inner diameter of about 5 mm to about 25 mm, more typically in the range of about 8 mm to about 20 mm.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and modifications in the illustrated device and method, and further applications of the principles of the invention as illustrated therein are herein contemplated as would normally occur to one skilled in the art to which the invention relates are included.

Figure 1B:
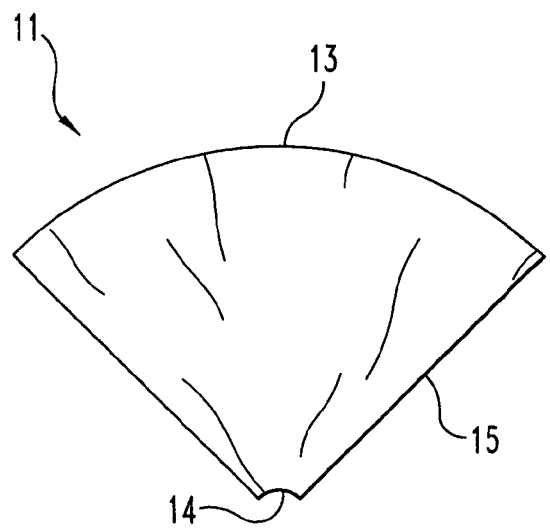
FIG. 1B provides a perspective view of one of the frameless prosthetic valve devices taken from the sheet in FIG. 1A.
Figure 1C:
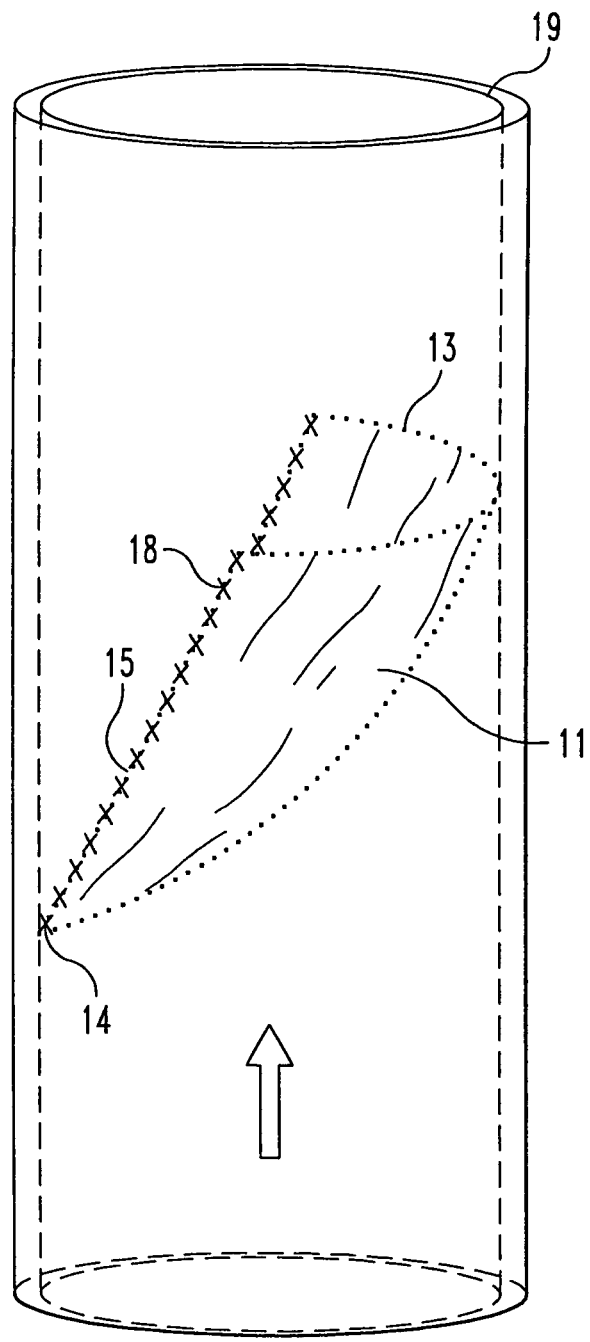
FIG. 1C provides a cutaway view of a bodily passage having a frameless prosthetic valve device of the invention attached thereto.

With reference now to FIG. 1A, illustrated is a sheet of an extracellular matrix composite 12 including a first extracellular matrix material having a surface 16, and a second, biosynthetically-deposited extracellular matrix material 17 on said surface 16 from which four frameless prosthetic valve devices can be formed. FIG. 1B illustrates one of these four frameless prosthetic valve devices. Frameless prosthetic valve device 11 comprises a top edge 13, a base 14, and diverging sides 15 extending from the base edge to the top edge. Typically, the top edge 13, base 14, and diverging sides 15 are constructed so as to have specific dimensions for optimal performance when attached to a vein. Frameless prosthetic valve device 11 can be attached to a bodily passage so as to allow for antegrade blood flow while restricting retrograde blood flow. The direction of antegrade blood flow is represented by the arrow depicted in FIG. 1C. The frameless prosthetic valve device can be stitched 18 along base 14 and diverging sides 15 to an inner wall 19 of a bodily passage (e.g., a vascular passage) such that top edge 13 is free to open and close as a result of vascular pressure. As will be understood, a prosthetic valve device such as 11 can be dimensioned for use alone as a monocusp valve, or can be dimensioned for use with one or more additional similar prostheses to provide a multicusp valve.

Figure 2:
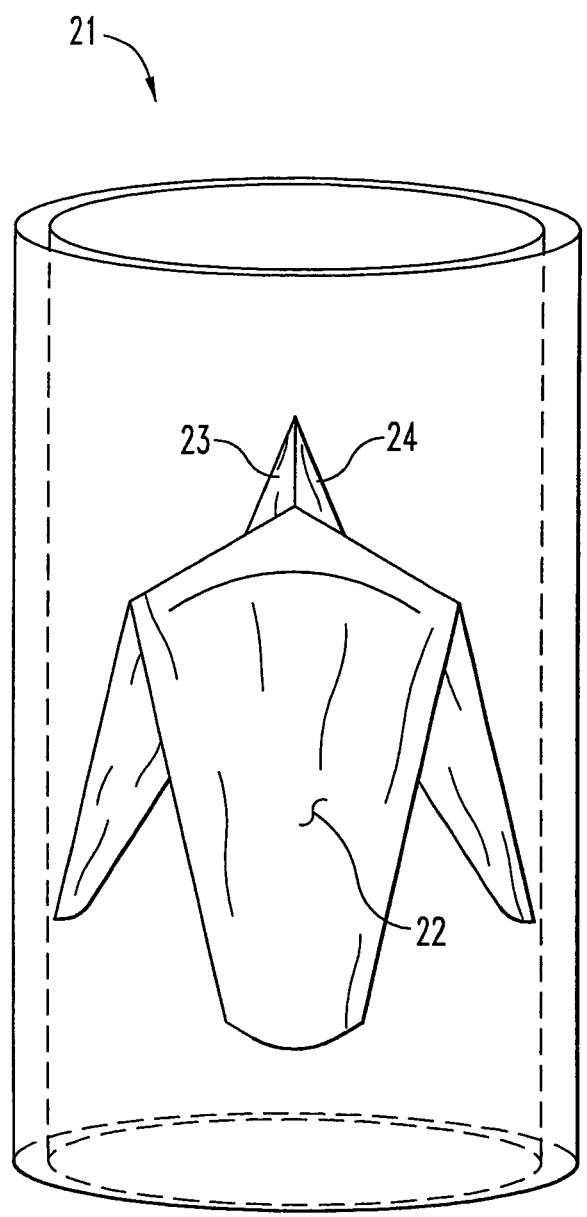
FIG. 2 provides a cutaway view of a bodily passage having a multi-cuspid frameless prosthetic valve device of the invention attached thereto.

With reference to FIG. 2, shown is a cutaway view of a bodily passage having a multi-cusp frameless prosthetic valve device of the invention attached therein. In particular, shown is a frameless tricuspid valve 21, generally having cusps 22, 23 and 24. Valve 21 can be provided in the vessel as a single, integral piece having material constituting cusps 22, 23 and 24 and slits in appropriate locations to provide the illustrated tricuspid orifice, or can be provided with multiple pieces of the extracellular matrix composite, e.g. three pieces with a separate piece providing each of cusps 22, 23 and 24. It will be understood that similar considerations will apply to other multicusp valves of the invention, including bicusp, quadricusp, etc., valves. As well, it will be understood that any suitable method of attaching the edges of the prosthesis to the vessel wall may be used, including for example those disclosed hereinabove.

Figure 3:
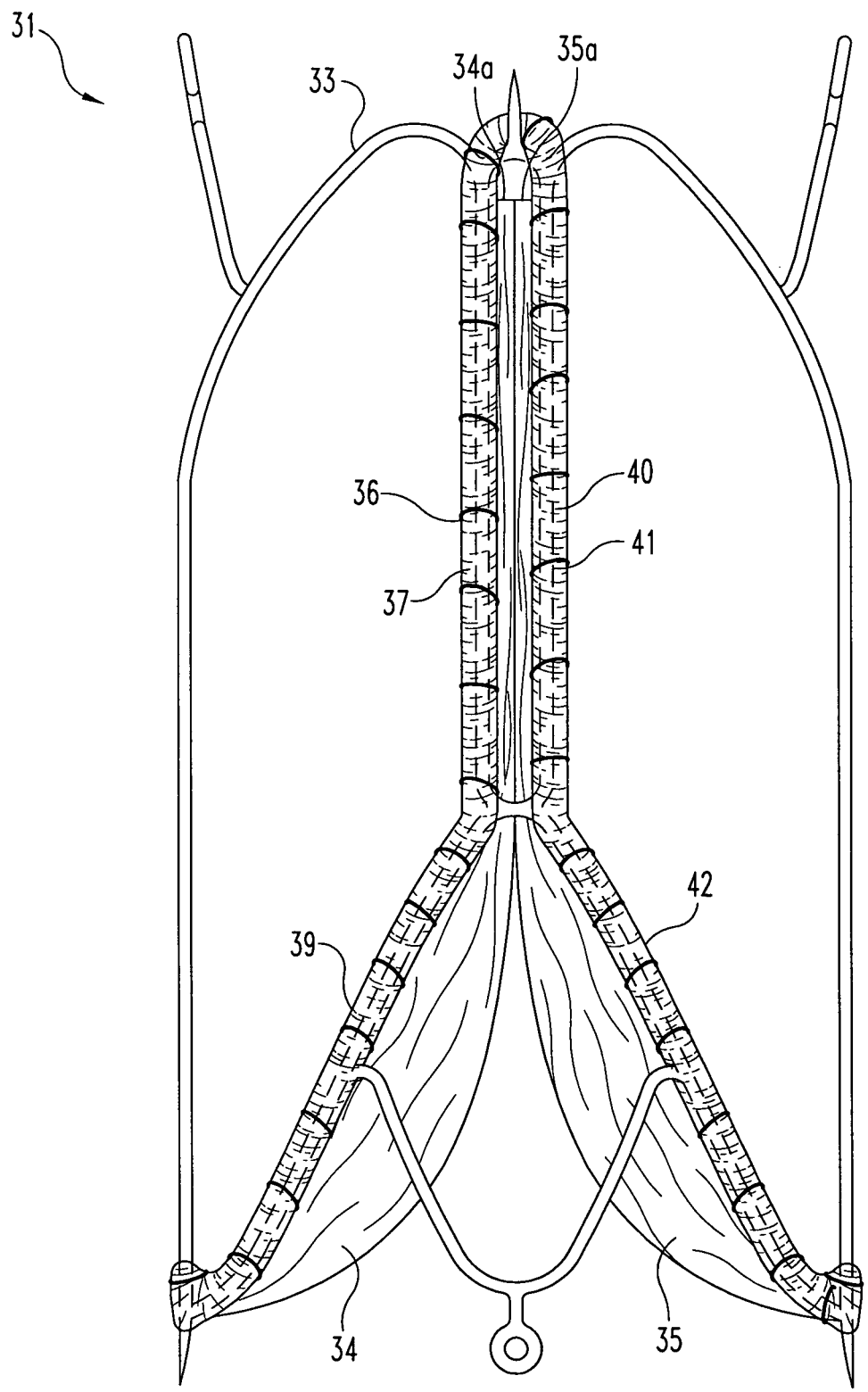
FIG. 3 provides a side view of one prosthetic valve device of the invention that includes an extracellular matrix composite attached to a frame. The extracellular matrix composite includes a first extracellular matrix material having a surface, and a second extracellular matrix material deposited on said surface.
Figure 4:
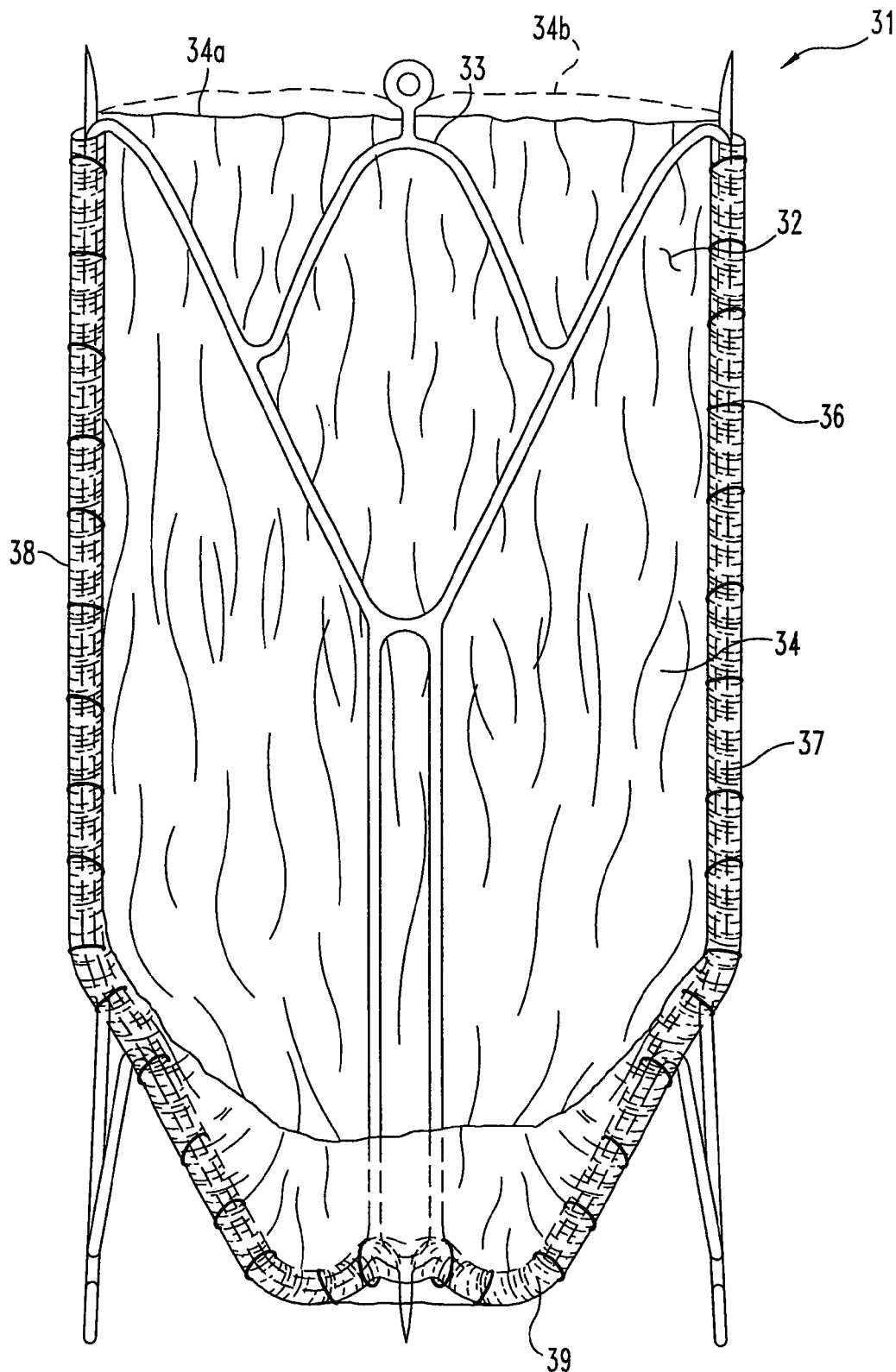
FIG. 4 provides a left side view of the prosthetic valve device depicted in FIG. 3.
Figure 5:
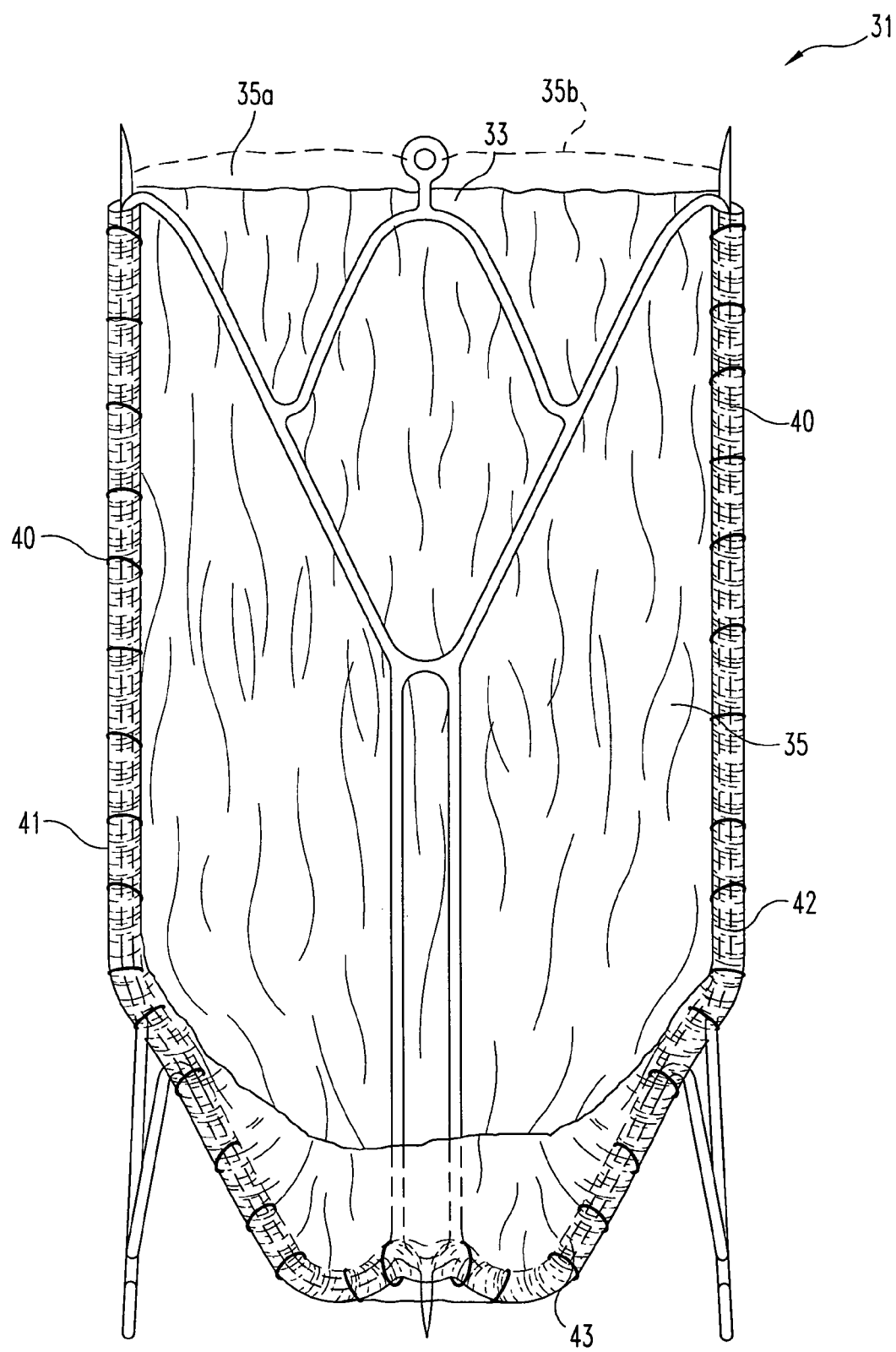
FIG. 5 provides a right side view of the prosthetic valve device depicted in FIG. 3.

With reference now to FIGS. 3-5, depicted are various side views of a prosthetic valve device 31 of the invention. The extracellular matrix composite is attached to a frame element 33 and provides two leaflets 34 and 35 in an original configuration for implantation in a patient. In particular, FIG. 3 provides a side view of prosthetic valve device 31 taken in a direction parallel to the coapting upper edges 34a and 35a of leaflets 34 and 35. FIG. 4 provides a view of the device 31 depicted in FIG. 3 taken from the left side. FIG. 5 provides a view of the device 31 depicted in FIG. 3 taken from the right side. Device 31 is particularly well suited for vascular applications, such as implantation into a vascular passage of a patient.

As can be seen from FIGS. 3-5, leaflets 34 and 35 include respective free edges 34a and 35a for coaptation with one another and respective fixed edges 36 and 40 that will each be forced against the wall of a vascular vessel upon implantation of device 31 in a path that partially circumscribes the vessel wall so as to each form a blood-capturing element. In the device 31 illustrated, the path of leaflet edge contact with the vessel wall includes substantial portions that extend essentially longitudinal along the vessel wall that connect to a cup-forming portion that extends both longitudinally along the vessel wall and circumferentially around the vessel wall. In particular, the fixed edge 36 of leaflet 34 includes opposite longitudinally-extending portions 37 and 38 each extending to an opposite side of a cup-forming portion 39. Correspondingly, the fixed edge 40 of leaflet 35 includes opposite longitudinally-extending portions 41 and 42 each extending to an opposite side of cup-forming portion 43.

The amount of contacting or coapting leaflet area can be expressed in a number of different ways. The length of coaptation (e.g., LOC) in the original configuration for implant is desirably at least about 2 mm and may be as much as about 50 mm or more depending on the configuration of the valve prosthesis. In certain embodiments of the invention, the length of coaptation can be within the range of about 5 to about 30 mm, more typically about 5 to about 15 mm, in the original configuration for implant. The length of coaptation can represent a substantial percentage of the overall length of the valve prosthesis, for example, at least about 5%, or at least about 10%, of the overall length of the prosthesis. In certain embodiments, the length of coaptation of the leaflets represents 10% to 80% of the length of the overall device, typically about 30% to about 60%, and more typically about 35% to about 55%.

In additional aspects of the invention, a long length of coaptation can be provided by orienting the outer leaflet edges substantially longitudinally along the frame in close proximity to one another over a significant distance. Thus, with reference to FIGS. 3-5 for purposes of illustration, outer leaflet edge portion 37 of leaflet 34 is configured to contact along the vessel wall in close proximity to outer leaflet edge portion 41 of leaflet 35 over a significant distance, for example 2 to 50 mm, typically about 5 to about 30 mm, and more typically about 5 to about 15 mm. The same would be true for the leaflet edge portions tracking along the opposite side of the vessel wall (e.g., edge portions 38 and 42, FIGS. 3-5). It is preferred that the leaflet edges remain in close proximity over these distances, for example within about 5 mm, more preferably within about 3 mm, and most preferably within about 1 mm. It will be understood that this close proximity may involve having leaflet edges track closely with one another along the vessel wall, or may have them being attached along essentially the same path (e.g., both along a single strut of a frame) and thus exhibiting essentially no separation from one another as they pass along the vessel wall.

As disclosed above, the present invention provides prosthetic valve devices including extracellular matrix composites, and methods for their manufacture and use. As used herein, the term "acellular" means free or essentially free from living cells. The term "substantially devoid of cells and cell components" means free or essentially free from cells (living or dead) and of cell membranes and other cell remnants. An ECM material substantially devoid of cells or cell components is intended to include the ECM material carrying cells or cell components at a level sufficiently low to be non-immunogenic when the material is implanted in a recipient, especially a recipient to which the cells or cell components are xenogenic or allogenic. The term "decellularizing" in respect of a cell-containing ECM material means that the material is treated to as to remove at least about 70% of the original cells (living or dead). More preferably, at least 90% of the cells will be removed, and most preferably at least 99% of the cells will be removed, in decellularization processes involved in the instant invention.

Prosthetic valve devices and methods of the invention employ a first extracellular matrix (ECM) base material. Preferred are naturally-derived collagenous ECMs isolated from suitable animal or human tissue sources. Suitable extracellular matrix materials include, for instance, submucosa (including for example small intestinal submucosa, stomach submucosa, urinary bladder submucosa, or uterine submucosa, each of these isolated from juvenile or adult animals), renal capsule membrane, amnion, dura mater, pericardium, serosa, peritoneum or basement membrane materials, including liver basement membrane or epithelial basement membrane materials. These materials may be isolated and used as intact natural sheet forms, or reconstituted collagen layers including collagen derived from these materials and/or other collagenous materials may be used. For additional information as to submucosa materials useful in the present invention, and their isolation and treatment, reference can be made to U.S. Pat. Nos. 4,902,508, 5,554,389, 5,733,337, 5,993,844, 6,206,931, 6,099,567, and 6,331,319. Renal capsule membrane can also be obtained from warm-blooded vertebrates, as described more particularly in International Patent Application serial No. PCT/US02/20499 filed Jun. 28, 2002, published Jan. 9, 2003 as WO 03/002165.

Preferred ECM base materials for use in the invention contain residual bioactive proteins or other ECM components derived from the tissue source of the materials. For example, they may contain Fibroblast Growth Factor-2 (basic FGF), Transforming Growth Factor-beta (TGF-beta), vascular endothelial growth factor (VEGF), epidermal growth factor (EGF) and/or platelet derived growth factor (PDGF). It is also expected that ECM base materials of the invention may contain additional bioactive components including, for example, one or more of glycosaminoglycans, glycoproteins, proteoglycans, and/or growth factors. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics, thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

In accordance with one embodiment of the invention, cells will be cultured in vitro on the ECM material under conditions and for a duration wherein secreted extracellular matrix proteins are deposited upon a portion of or the entire surface of the ECM material. After deposition of the desired amount of extracellular matrix proteins, the resulting ECM composite material can be isolated by decellularizing the material. The deposited ECM proteins may, for example, enhance the functionality of the ECM base material, e.g. by potentially affecting remodeling of the material by cells and/or the thrombogenicity of the material. In addition, after seeding, e.g. during culture, the ECM base material along with seeded cells can be subjected to mechanical, chemical or physical stresses to influence the cell growth and deposition products. Such forces could include but are not limited to mechanically stretching the ECM base material, preferably without tearing it, subjecting the ECM base material to pulsatile forces (e.g. by flowing fluid such as culture medium through a tube of ECM base material), altering the culture atmosphere, e.g. to a higher or lower carbon dioxide content, or adding specific growth factors or chemokines that affect the cell growth rates, phenotypes, secretory functions or apoptosis events, thereby affecting the molecules deposited by the cells.

Cells to be used to secrete ECM proteins can be applied to the surface of the base ECM supporting structure in any suitable fashion. Illustratively, the cells can be applied to the base ECM material by allowing gravity to settle the cells onto the base ECM. Positive pressure may also be used to force media through the ECM material, thereby depositing cells onto the ECM surface. Other suitable means for applying the cells to the ECM may include, but not be limited to using negative pressure to draw the cells onto the ECM material; and using chemotactic agents, for example.

As to the type and source of the cells to be used to deposit ECM components onto the ECM base material, a variety of cell types, or combinations of cell types, may be used. These cell types are known to those of ordinary skill in the art, as are appropriate conditions for their culture. Illustratively, cell types to produce the ECM proteins for deposition include vascular and other endothelial cells (including microvascular endothelial cells), vascular and other smooth muscle cells, fibroblasts, corneal endothelium or epithelium, glomerular epithelium, and mesothelial cells, pericytes, macrophages, monocytes, plasma cells, mast cells, adipocytes, chondrocytes, etc. These other cells can be readily derived from appropriate organs or tissues such as skin, liver, etc., using methods known, such as those discussed above. Alternatively or in addition, cells from established cell lines of any of the above-mentioned or other suitable types may be used to deposit the ECM components. Cells of cardiovascular origin, and in particular vascular endothelial cells, are preferred, used alone or in combination with vascular smooth muscle cells.

Illustratively, vascular smooth muscle cells (SMCs) can be isolated from segments of carotid or femoral arteries obtained from humans (e.g. the patient to be treated or cadaver) or animals. Such isolation procedures are known and may for example involve storing the tissue segments in a suitable sterile medium, such as sterile Medium 199 (Gibco BRL) potentially also containing antibiotic agents such as gentamicin. The artery segment can be slit longitudinally and the endothelial cells removed by rubbing and/or scraping (e.g. with a scalpel blade). Thin strips of arterial media peeled up with forceps are pooled into HBSS in a sterile Petri dish. The strips can then be cultured in tissue culture flasks containing a suitable culture medium, e.g. Smooth Muscle Cell Growth Medium (SMCGM) (43% Dulbecco's Modified Eagle Medium (DMEM); 43% Medium 199; 13% fetal bovine serum; 2 mM glutamine; 15 units/ml heparin; 23 µg/ml gentamicin; and 12.5 µg/ml endothelial cell growth supplement (Collaborative Biomedical Products, Bedford, Mass.)). The culture medium can be replaced when significant outgrowth of cells from the tissue pieces is observed. The cells can then be fed the SMCGM periodically as needed, and conventionally passaged and split. Smooth muscle cell type can be confirmed, for instance by morphological criteria, positive staining for alpha smooth muscle cell actin, and/or other suitable known techniques.

For seeding purposes, subconfluent VSMC cultures can be rinsed with calcium-magnesium-free-HBSS (CMF-HBSS) and washed in CMF-HBSS. Cells can be harvested using trypsin-ethylenediamine tetraacetic acid (EDTA) to release cells from the flask, followed by trypsin neutralization with SMCGM. Cells can be pelleted by centrifugation and the pellet re-suspended in SMCGM for cell counting. After centrifugation, the cell pellet can be re-suspended in SMCGM. This cell suspension can then be contacted with the ECM base material to seed the material with the cells. The seeded ECM can then be placed into a culture container filled with SMCGM. The culture container can be capped and incubated at about 37° C. on a roller apparatus. The medium in the culture tubes can be periodically replaced and the seeded ECMs can be cultured for a period sufficient to deposit ECM components, for example, from one to twenty days.

In another embodiment, endothelial cells are used to deposit ECM proteins on an ECM base material. For instance, endothelial cells can be caused to attach and spread on the ECM surface, and cultured to deposit the ECM proteins. For these purposes, small patches of endothelial cells may be directly harvested from a donor vessel (e.g. a vessel of the patient to be treated, or a cadaver) and seeded onto an ECM surface whereby they will attach and proliferate to cover the ECM surface, and deposit ECM components.

In one mode of recovery, enzymatic methods can be used to release endothelial cells (ECs) from arterial or venous vessels obtained from humans or animals. The vessel lumina are cannulated, rinsed with HBSS, and filled with an endothelial cell harvesting enzyme solution in a suitable medium such as CMF-HBSS. Suitable enzymes include, but are not limited to, collagenase, dispase, and trypsin. Endothelial cells are flushed into a sterile centrifuge tube and the ECs pelleted. The cells are then plated onto tissue culture flasks, grown at about 37° C. until nearly confluent and then passaged. Endothelial cell type can be confirmed by morphological criteria, by positive staining for Factor VIII, and by uptake of acetylated low density lipoprotein.

Subconfluent endothelial cells (passages 2-10, for example) can be rinsed with CMF-HBSS and washed in CMF-HBSS. The cells can be harvested by using trypsin-EDTA to release cells from the flasks followed by trypsin neutralization with complete Endothelial Cell Growth Medium (ECGM; 80% Medium 199, 16% fetal bovine serum, 2 mM glutamine, 15 units/ml heparin, 25 µg/ml gentamicin, 12.5 µg/ml Endothelial Cell Growth Supplement (Collaborative Biomedical Products, Bedford, Mass.)). The cells can be pelleted and the pellet re-suspended in ECGM. This suspension can then be used to seed the ECM base material, and then cultured in association with the ECM base material to secrete and deposit the desired amount of ECM components, for example, one to twenty days.

Once a suitable layer of secreted ECM proteins is created, the endothelial cell layer can be removed. For example, the endothelial cells can be removed by rinsing the graft several times (e.g. three times) with HBSS, and treating with an ammonium hydroxide solution, e.g. about 0.025M ammonium hydroxide, to remove the endothelial cells, and rinsed again several times in HBSS. Other suitable treatments may include, for example, 0.01-0.5M ammonium hydroxide for about 30 seconds to about 60 minutes. Other candidate methods of removing the endothelial cells may include air drying, or treatment with other stripping solutions, for example, chloroform, methanol, ammonium hydroxide, or sodium chloride, either alone or in combination. Other treatments known to those skilled in the art may also be suitable.

It is also possible to produce a secreted matrix deposit through a variety of other methods. One suitable method, for example, involves using mixed culture seeding in which both ECs and SMCs are combined and both cell types are seeded onto the ECM base material simultaneously. After extended co-culture, the secreted matrix will be produced.

Fibroblasts for use in depositing extracellular matrix proteins may be readily isolated from an appropriate source organ or tissue. This can be readily accomplished using techniques known to those skilled in the art. For example, the tissue or organ can be disaggregated mechanically and/or treated with digestive enzymes and/or chelating agents that weaken the connections between neighboring cells, making it possible to disperse the tissue into a suspension of individual cells without appreciable cell breakage. Enzymatic dissociation can be accomplished by mincing the tissue and treating the minced tissue with any of a number of digestive enzymes either alone or in combination. Such enzymes include, but are not limited to, trypsin, chymotrypsin, collagenase, elastase, hyaluronidase, DNase, pronase, and/or dispase etc. Mechanical disruption can also be accomplished by a number of methods including, but not limited to the use of grinders, blenders, sieves, homogenizers, pressure cells, insonators, and the like.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting.

In one embodiment of the present invention, cells, which are specialized for the particular tissue implant site, can be cultured on the base ECM material for the production of a tissue type specific extracellular matrix composite. Accordingly, the first ECM material can conditioned to create the ECM composite using cells of a given type, and the resulting ECM composite can be configured for and grafted on or in a type of tissue of the patient having cells of that given type.

For example, dermal fibroblasts can be used to form the three-dimensional subconfluent stroma for the production of skin-specific extracellular composite matrix in vitro. Alternatively, stromal cells of hematopoietic tissue including, but not limited to, fibroblast endothelial cells, macrophages/monocytes, adipocytes and reticular cells, can be used to form the three-dimensional subconfluent stroma for the production of a bone marrow-specific extracellular matrix in vitro. Hematopoietic stromal cells can be readily obtained from the "buffy coat" formed in bone marrow suspensions by centrifugation at low forces, e.g., 3000× g.

Similarly, glial cells can be used as the stroma to support the proliferation of neurological cells and tissues. Glial cells for this purpose can be obtained by trypsinization or collagenase digestion of embryonic or adult brain.

For certain uses in vivo it may be preferable to obtain the cells from the subject's own tissues. The growth of cells in the presence of the ECM base material can be further enhanced by adding to the framework, or coating the framework support with natural or recombinant molecules, including but not limited to, proteins, such as collagens, elastic fibers, reticular fibers, and glycoproteins; glycosaminoglycans, such as heparin sulfate, chondroitin-4-sulfate, chondroitin-6-sulfate, dermatan sulfate, keratan sulfate, etc.; a cellular matrix, and/or other materials, such as whole blood, serum, growth factors, fibronectin, Pronectin F, RGD peptide, or cell or tissue extracts.

Stem cells may also be used and cultured on the ECM base material to deposit extracellular matrix components. Illustratively, adult or embryonic stem cells may be cultured and treated with appropriate differentiation factors to mature and secrete extracellular matrix components. The differentiated cell population can then be removed using suitable techniques as described herein.

After inoculation with the cells, the ECM base material is incubated in an appropriate nutrient medium under physiologic conditions favorable for cell growth, i.e., promoting mitosis (cell division). Many commercially available media such as RPMI 1640, Fisher's, Iscove's, McCoy's, and the like, may be suitable for use. The three-dimensional culture can be suspended or floated in the medium during the incubation period in order to maximize proliferative activity. In addition, the culture can be "fed" periodically to remove the spent media, depopulate released cells, and to add fresh media.

During the incubation period, the cells are grown to an appropriate degree to allow for adequate deposition of extracellular matrix components. The extracellular matrix components are secreted locally by cells and not only bind cells and tissues together but also influence the development and behavior of the cells they contact. The typical extracellular matrix contains various fiber-forming proteins interwoven in a hydrated gel composed of a network of glycosaminoglycan chains. The glycosaminoglycans are a heterogeneous group of long, negatively charged polysaccharide chains, which (except for hyaluronic acid) are covalently linked to protein to form proteoglycan molecules.

The fiber-forming proteins are of two functional types: (a) mainly structural (collagens and elastin), and (b) mainly adhesive (such as fibronectin and laminin). The fibrillar collagens (types I, II, and III) are rope-like, triple-stranded helical molecules that aggregate into long cable-like fibrils in the extracellular space; these in turn can assemble into a variety of highly ordered arrays. Type IV collagen molecules assemble into a sheet-like meshwork that forms the core of all basal laminae. Elastin molecules form an extensive cross-linked network of fibers and sheets that can stretch and recoil, imparting elasticity to the matrix.

Fibronectin and laminin are examples of large adhesive glycoproteins in the matrix; fibronectin is widely distributed in connective tissues, whereas laminin is found mainly in basal laminae. By means of their multiple binding domains, such proteins help cells adhere to and become organized by the extracellular matrix.

As an example, a naturally secreted human dermal extracellular matrix contains type I and type III collagens, fibronectin, tenascin, glycosaminoglycans, acidic and basic FGF, TGF-beta, KGF, decorin and various other secreted human dermal matrix proteins. As naturally secreted products, the various extracellular matrix proteins are produced in the quantities and ratios similar to that existing in vivo. Moreover, growth of the stromal cells in three dimensions will sustain active proliferation of cells in culture for much longer time periods than will monolayer systems. Further, the three-dimensional system supports the maturation, differentiation, and segregation of cells in culture in vitro to form components of adult tissues analogous to counterparts found in vivo. Thus, the extracellular matrix created by the cells in culture is more analogous to native tissues.

As disclosed above, the ECM composite material will be decellularized after deposition of the desired level of non-native ECM components on the ECM base material. In an illustrative decellularization process, the tissue may be treated with a solution that releases component cells from the associated extracellular membrane matrix. There are a number of agents and methods that will remove the cells. The cell-containing composite material can be treated with a mild chemical stripping solution, such as ammonium hydroxide ($NH_4OH$). One such treatment may involve incubating the material in an aqueous $NH_4OH$ solution at a concentration of about 0.01M to about 0.5M, for a period of about 30 seconds to about 60 minutes followed by flushing the vessel lumen or other ECM construct with a buffer solution. Illustratively, the treatment may involve treating the cell-containing material with a 0.25M $NH_4OH$ solution for about 1 to 10 minutes.

Decellularization may also involve air drying. Following air drying, the material can be flushed with buffer to remove cells and cell components and rehydrate the ECM composite for further processing, if desired.

The cells can also be removed by exposing the cell-containing material to one or more freeze-thaw cycles, typically followed by removal of dead cells and cell debris. For example, such removal may be accomplished by flushing the material after freezing with a suitable solution such as HBSS (1.3 mM $CaCl_2$, 5 mM KCl, 0.3 mM $KH_2PO_4$, 0.5 mM $MgCl_2$, 0.4 mM $MgSO_4$, 138 mM NaCl, 4 mM $NaHCO_3$, 0.3 mM $NaHPO_4$, 5.6 mM glucose). Freeze-kill of the cells may be accomplished, for instance, by flash-freezing the living cells in liquid nitrogen.

The cells may also be killed by irrigating the inoculated three-dimensional framework with sterile water, such that the cells burst in response to osmotic pressure. Once the cells have been killed, one can, for example, disrupt the cellular membranes and remove the cellular debris by a mild detergent rinse, such as EDTA, CHAPS or a zwitterionic detergent, followed by treatment with a cryoprotectant such as DMSO, propylene glycol, butanediol, raffinose, polyvinyl pyrrolidone, dextran or sucrose and vitrified in liquid nitrogen.

Alternatively, the cell-containing material can be subjected to enzymatic digestion and/or extracting with reagents that break down the cellular membranes and allow removal of cell contents. Examples of detergents include non-ionic detergents (for example, TRITON X-100, octylphenoxy polyethoxyethanol, (Rohm and Haas); BRIJ-35, a polyethoxyethanol lauryl ether (Atlas Chemical Co.), TWEEN 20, a polyethoxyethanol sorbitan monolaureate (Rohm and Haas), LUBROL-PX, or polyethylene lauryl ether (Rohm and Haas)); and ionic detergents (for example, sodium dodecyl sulphate, sulfated higher aliphatic alcohol, sulfonated alkane and sulfonated alkylarene containing 7 to 22 carbon atoms in a branched or unbranched chain). Enzymes can be used also and can include nucleases (for example, deoxyribonuclease and ribonuclease), phospholipases and lipases.

Following removal of the cells, the ECM composite material can be treated with a fixative, if desired. This fixation can be accomplished by placing the graft into a fixing solution, such as, for example, glutaraldehyde in a suitable buffer. Suitable buffers may include, but are not limited to, N-2-hydroxyethylpiperazine-N'-2-ethane sulfonic acid (HEPES), acetate, 2-(N-morpholino) ethanesulfonic acid (MES), 3-[N-morpholino]propanesulfonic acid (MOPS), tris hydroxymethyl aminomethane, phosphate, and others. Any remaining aldehyde reactive sites can be blocked with an amino group containing solution. Suitable reagents for this procedure include, but are not limited to, 0.1M glycine, Medium 199, Dulbecco's Modified Eagle Medium, and other physiological culture media, for example.

Following removal of the cells used to deposit the second extracellular matrix material, the isolated extracellular matrix composite material can be used to prepare a cell-seeded graft, if desired. For example, cells allogenic or autogenic to the recipient of a graft of the composite material can be seeded and optionally proliferated on the composite material, which can then be implanted, along with the cells, into the recipient. Any of the cell types disclosed above for deposit of the second extracellular matrix material can also be used in such cell-seeded grafts, including combinations of such cell types. In certain embodiments of cell-seeded grafts, the first extracellular matrix material will be xenogenic to a human recipient (e.g. of porcine or bovine origin), the second extracellular matrix material will be human but allogenic to the recipient, and the cells of the cell-seeded graft will be autogenic or allogenic to the recipient, and when allogenic optionally either immunologically matched or modulated to minimize potential immune response.

Devices of the invention are desirably adapted for deployment within the vascular system, and in particularly preferred embodiments, devices of the invention are adapted for deployment within the venous system. Accordingly, preferred devices, such as devices 11, 21 and 31 are adapted as venous valves, for example for percutaneous implantation within veins of the legs or feet, to treat venous insufficiency.

The prosthetic valve devices of the invention can be attached to a bodily in any suitable manner. Typically, the manner in which the valve device is attached to a bodily passage will depend on the type of valve device employed. Preferably, the frameless grafting prosthesis is attached to a wall of a vein or other vascular vessel surgically. Such a surgical procedure typically comprises suturing or otherwise physically connecting the edges of the at least one shaped valve cusp of the frameless grafting prosthesis to the luminal surface of a vein or other vascular vessel. Other potential surgical attachment procedures include, for example, stapling, bonding or otherwise adhering the edges of the at least one shaped valve cusp of the frameless grafting prosthesis to the luminal surface of a vein or other vascular vessel.

Where the inventive prosthesis is to be used to provide venous valve, the prosthesis can be implanted above, below, or at the location of a native venous valve in the patient. Moreover, a plurality of the grafting prosthesis devices can be implanted in a given vein, to treat venous insufficiency or other similar disorders.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

What is claimed is:

1. A prosthetic valve device for implantation in a bodily passage, comprising:
   an artificial valve comprising a frame and at least two leaflets attached thereto, wherein said leaflets include a first leaflet and a second leaflet formed with an extracellular matrix composite material including a first extracellular matrix material having a surface, and a second, biosynthetically-deposited extracellular matrix material including extracellular matrix proteins on said surface, said biosynthetically-deposited extracellular matrix material having been deposited on said first extracellular matrix material by cells cultured on said first extracellular matrix material followed by removal of said cells to provide said extracellular matrix composite material;
   wherein said extracellular matrix proteins enhance the function of said first extracellular matrix material in each said leaflet by modifying the thrombogenicity and remodeling of the first extracellular matrix material;
   wherein said artificial valve has a length of coaptation in the range of about 5 to 30 mm;
   wherein said first leaflet and said second leaflet each include a first outer edge;
   wherein the first outer leaflet edges of the first and second leaflets are within about 3 mm of one another as they extend in a longitudinal direction along said frame for a distance of about 5 to about 30 mm; and
   wherein the valve device is configured such that at least a portion of said outer leaflet edges extending in a longitudinal direction contact the bodily passage when the valve device is implanted in the bodily passage.

2. The prosthetic valve device of claim 1, wherein said second extracellular matrix material comprises one or more fiber-forming proteins.

3. The prosthetic valve device of claim 2, wherein the one or more fiber-forming proteins include collagen and/or elastin.

4. The prosthetic valve device of claim 1, wherein said second extracellular matrix material comprises one or more adhesive proteins.

5. The prosthetic valve device of claim 4, wherein said adhesive proteins comprise fibronectin and/or laminin.

6. The prosthetic valve device of claim 1, wherein the first extracellular matrix material comprises submucosa.

7. The prosthetic valve device of claim 6, wherein the submucosa is intestinal, urinary bladder or stomach submucosa.

8. The prosthetic valve device of claim 7, wherein the submucosa is small intestinal submucosa.

9. The prosthetic valve device of claim 1, wherein the first extracellular matrix material is from a warm-blooded vertebrate.

10. The prosthetic valve device of claim 1, wherein the second extracellular matrix material is human.

11. The prosthetic valve device of claim 1, wherein the second extracellular matrix material is secreted by one or more of endothelial cells, muscle cells, fibroblast cells, mesothelial cells, pericyte cells, macrophage cells, monocyte cells, plasma cells, mast cells, adipocyte cells, chondrocyte cells, stem cells, or a cell population differentiated from stem cells.

12. The prosthetic valve device of claim 11, wherein the second extracellular matrix material contains matrix components secreted by endothelial cells.

13. The prosthetic valve device of claim 12, wherein the endothelial cells are vascular endothelial cells.

14. The prosthetic valve device of claim 13, wherein said device is configured for implantation in the cardiovascular system of a human.

15. The prosthetic valve device of claim 1, wherein said first outer leaflet edges are fixedly attached to said frame over said distance.

16. The prosthetic valve device of claim 1, wherein said extracellular matrix composite is substantially devoid of cells or cell components.

17. The prosthetic valve device of claim 1, wherein said device is configured for vascular applications.

18. A method for treating a patient, comprising:
providing a prosthetic valve device of claim 1 and implanting said prosthetic valve device into a bodily passage of the patient.

19. The method of claim 18, wherein said prosthetic valve device is configured for use in vascular applications.

20. The method of claim 19, wherein said patient is treated for a vascular disease by implanting said valve device into a vascular passage of the patient.

21. The method of claim 20, wherein said patient is treated for valvular insufficiency.

22. A prosthetic valve device for implantation in a bodily passage, comprising:
an artificial valve comprising a frame and at least two leaflets attached thereto, wherein said leaflets include a first leaflet and a second leaflet formed with a decellularized extracellular matrix composite sheet material including a first extracellular matrix material having a surface, and a second, biosynthetically-deposited extracellular matrix material on said surface, wherein said biosynthetically-deposited extracellular matrix material has been deposited on said surface by culturing cells on the first extracellular matrix to deposit extracellular matrix proteins including fiber-forming proteins interwoven in a hydrated gel composed of a network of glycosaminoglycan chains, followed by removal of the cells to provide said decellularized extracellular matrix composite sheet material;
wherein said extracellular matrix proteins enhance the function of said first extracellular matrix material in each said leaflet by modifying the thrombogenicity and remodeling of the first extracellular matrix material;
wherein said artificial valve has a length of coaptation in the range of about 5 to 30 mm;
wherein said first leaflet and said second leaflet each include a first outer edge fixedly attached to the frame and a second outer edge fixedly attached to the frame, a first face spanning between the first outer edge and the second outer edge, and a second face opposite the first face and spanning between the first outer edge and the second outer edge;
wherein the first outer leaflet edges of the first and second leaflets are within about 3 mm of one another as they extend in a longitudinal direction along said frame for a distance of about 5 to about 30 mm; and
wherein the valve device is configured such that at least a portion of said first outer leaflet edges extending in a longitudinal direction contact the bodily passage when the valve device is implanted in the bodily passage.

23. The prosthetic valve device of claim 22, wherein the fiber-forming proteins include collagen and/or elastin.

24. The prosthetic valve device of claim 22, wherein said second extracellular matrix material comprises fibronectin and/or laminin.

25. The prosthetic valve device of claim 22, wherein the first extracellular matrix material comprises submucosa.

26. The prosthetic valve device of claim 25, wherein the submucosa is intestinal, urinary bladder or stomach submucosa.

27. The prosthetic valve device of claim 26, wherein the submucosa is small intestinal submucosa.

28. The prosthetic valve device of claim 22, wherein the first extracellular matrix material is from a warm-blooded vertebrate.

29. The prosthetic valve device of claim 22, wherein the second extracellular matrix material is human.

30. The prosthetic valve device of claim 22, wherein the second extracellular matrix material is secreted by one or more of endothelial cells, muscle cells, fibroblast cells, mesothelial cells, pericyte cells, macrophage cells, monocyte cells, plasma cells, mast cells, adipocyte cells, chondrocyte cells, stem cells, or a cell population differentiated from stem cells.

31. The prosthetic valve device of claim 30, wherein the second extracellular matrix material contains matrix components secreted by endothelial cells.

32. The prosthetic valve device of claim 31, wherein the endothelial cells are vascular endothelial cells.

* * * * *